United States Patent [19]

Petro-Roy et al.

[11] Patent Number: 5,120,504

[45] Date of Patent: Jun. 9, 1992

[54] APPARATUS FOR IMMUNOASSAYS WITH VENT CHENNELS IN THE CONTAINER SIDE WALL

[75] Inventors: Virginia Petro-Roy; Kim D. Blickenstaff, both of San Diego, Calif.

[73] Assignee: Hybritech Incorporated, San Diego, Calif.

[21] Appl. No.: 378,477

[22] Filed: Jul. 12, 1989

Related U.S. Application Data

[63] Continuation of Ser. No. 885,129, Jul. 14, 1986, abandoned.

[51] Int. Cl.⁵ .......................................... G01N 21/77
[52] U.S. Cl. .................................. 422/58; 422/56; 422/60; 422/101; 422/102; 435/288; 435/291; 435/296
[58] Field of Search ................. 435/7, 5, 30, 291, 287, 435/292, 293, 294, 296, 311, 810, 288, 7.1; 436/807, 808, 815, 513, 518, 524, 527, 531, 548, 824; 422/56, 57, 60, 58, 101, 61, 102

[56] References Cited

U.S. PATENT DOCUMENTS

| | | | |
|---|---|---|---|
| 3,615,222 | 10/1971 | Mead | 23/230 |
| 3,645,687 | 2/1972 | Nerenberg | 23/230 |
| 3,715,192 | 2/1973 | Wenz et al. | 23/253 |
| 3,811,840 | 5/1974 | Bauer et al. | 23/253 |
| 3,825,410 | 7/1974 | Bagshawe | 23/230 |
| 3,843,324 | 10/1974 | Edelman et al. | 23/230 |
| 3,865,552 | 2/1975 | Marston | 436/810 X |
| 3,888,629 | 6/1975 | Bagshawe | 23/230 |
| 3,966,897 | 6/1976 | Renn et al. | 424/1.5 |
| 4,025,306 | 5/1977 | Studer | 435/30 X |
| 4,039,652 | 8/1977 | Adams et al. | 424/1 |
| 4,053,284 | 10/1977 | Posch | 23/259 |
| 4,061,468 | 12/1977 | Lange et al. | 23/253 |
| 4,094,647 | 6/1978 | Deutsch et al. | 23/253 |
| 4,138,474 | 2/1979 | Updike | 424/1 |
| 4,153,675 | 5/1979 | Kleinerman | 424/8 |
| 4,166,102 | 8/1979 | Johnson | 424/1 |
| 4,168,146 | 9/1979 | Grubb et al. | 23/230 |
| 4,180,383 | 12/1979 | Johnson | 422/69 |
| 4,193,983 | 3/1980 | Ullman et al. | 424/12 |
| 4,200,690 | 4/1980 | Root et al. | 435/7 |
| 4,235,601 | 11/1980 | Deutsch et al. | 23/230 |
| 4,246,339 | 1/1981 | Cole et al. | 435/7 |
| 4,305,924 | 12/1981 | Piasio et al. | 424/1 |
| 4,366,241 | 12/1982 | Tom et al. | 435/7 |
| 4,376,110 | 3/1983 | David et al. | 436/513 |
| 4,391,904 | 7/1983 | Litman et al. | 435/7 |
| 4,424,279 | 1/1984 | Bohn et al. | 436/534 |
| 4,425,438 | 1/1984 | Bauman et al. | 436/527 |
| 4,426,451 | 1/1984 | Columbus | 436/807 X |
| 4,477,578 | 10/1984 | Miles et al. | 436/810 X |
| 4,514,508 | 4/1985 | Hirschfeld | 436/518 |
| 4,563,417 | 1/1986 | Albarella et al. | 435/6 |
| 4,632,901 | 12/1986 | Valkirs et al. | 436/807 X |
| 4,727,019 | 2/1988 | Valkirs et al. | 435/287 |
| 4,999,163 | 3/1991 | Lennon et al. | 435/58 |

OTHER PUBLICATIONS

Gunars E. Valkirs and Richard Barton, "Immuno Concentration (TM—A New Format for Solid-Phase Immunoassays", Clinical Chemistry, vol. 31, No. 9, Sep., 1985, pp. 1427-1431.

Primary Examiner—Robert J. Warden
Assistant Examiner—William H. Beisner
Attorney, Agent, or Firm—Douglas J. Taylor; Leroy Whitaker; Paul C. Steinhardt

[57] ABSTRACT

Disclosed herein is an improved apparatus for conducting immunoassays. The apparatus comprises a container, and a test zone to which is bound an antibody, typically a monoclonal antibody, or which is capable of extracting cells from a fluid sample. The test zone may be a membrane, filter or a porous matrix in which microspheres to which are bound antibody are entrapped. The apparatus further comprises a liquid absorbing zone which is composed of absorbent material which acts when in contact with the test zone to induce flow through the test zone when a fluid sample is added to it. At least one port in communication with the liquid absorbing zone and the opening of the container is provided to allow gas displaced by the addition of fluid to be discharged from the container. The flow of the displaced gas being in a direction opposite to the flow of assay reagents through the liquid absorbing zone. Accordingly, the container can be entirely sealed from the environment by the use of a single removable seal over the opening of the container.

13 Claims, 1 Drawing Sheet

APPARATUS FOR IMMUNOASSAYS WITH VENT CHENNELS IN THE CONTAINER SIDE WALL

CROSS REFERENCE TO RELATED APPLICATIONS

This application is a continuation of application Ser. No. 885,129, filed on Jul. 14, 1986, now abandoned.

This application relates to subject matter of G. Valkirs et al., Ser. No. 609,395, filed May 11, 1984, now U.S. Pat. No. 4,632,901, issued Dec. 30, 1986, and its continuation-in-part, Ser. No. 733,292, filed May 10, 1985, now U.S. Pat. No. 4,727,019, issued Feb. 23, 1988. This application also relates to the subject matter of Rubenstein, Ser. No. 720,036, filed Apr. 4, 1985, now abandoned and its continuation-in-part, Ser. No. 847,799, filed Apr. 3, 1986, now abandoned, and its continuation-in-part Ser. No. 003,496, filed Jan. 15, 1987, now abandoned. The disclosures of all of the above commonly assigned references are hereby incorporated by reference herein.

FIELD OF THE INVENTION

This invention relates to immunoassays. In particular it relates to an improved apparatus and process used for conducting immunoassays.

BACKGROUND

For about two decades, immunoassay procedures have provided sensitive diagnostic tools for the in vitro detection of a variety of antigens associated with disease or other physical conditions of clinical significance. Originally such heterogeneous assays used a polyclonal antibody preparation bound to a solid phase. In these assays, a solution of labeled antigen is allowed to compete directly with antigen in the sample being analyzed for the solid phase antibody or is added to the antibody in a sequential process. The extent to which the labeled antigen is bound to the solid phase or is detected in the liquid phase can be used as a measure of the presence and quantity of antigen in the sample being analyzed.

Subsequently, non-competitive immunometric assays became available. In these assays, a polyclonal antibody preparation bound to a solid phase was also used. The sample containing the suspected antigen was allowed to contact the solid phase in order for the antigen to bind to the antibodies on the solid phase. Typically, after an incubation step the sample was separated from the solid phase which was then washed and incubated with a solution of additional polyclonal antibodies which had been labeled, for example with a radionuclide, an enzyme, or a fluorescent moiety.

After this second incubation, the unbound labeled antibody was separated from the solid phase and the amount of labeled antibody in either the liquid phase or bound to the solid phase in an antibody:antigen:antibody sandwich was determined as a measure of the presence and/or concentration of antigen in the sample tested.

More recently, immunoassay procedures have been modified to use monoclonal antibodies. For example, U.S. Pat. No. 4,376,110 describes two-sit immunometric assays using pairs of monoclonal antibodies, one bound to a solid phase and the other labeled to permit detection. The use of monoclonal antibody pairs which recognize different epitopic sites on an antigen has made it possible to conduct simultaneous immunometric assays in which the antigen and labeled antibody incubations do not require the intermediate washing steps of prior processes.

In the foregoing processes, the solid phase antibody is typically bound to a bead or small particles or coated on a surface. Alternatively, microspheres to which are bound antibody may be entrapped within a porous matrix. Recent improvements have drastically reduced the time necessary for the performance of the assays. As a result simpler and more rapid procedures for conducting immunoassays which employ a relatively simple apparatus make such assays available for use in the physician's office and even for over-the-counter sale to lay persons for use in home health care programs. For example, U.S. Pat. No. 3,811,840 describes a test device for detecting low concentrations of substances in test fluids comprising an adsorbant wick having a substantially flat surface portion enclosed in a fluid impervious sheath having an aperture of predetermined limited area formed therein. The aperture being contiguous to and exposing a predetermined limited area of the flat surface portion of the wick area. Within this aperture portion of the wick is incorporated a reagent specifically reactable with the substance being detected. In use, the device is dipped into the test fluid where the test fluid contacts the reagent area of the aperture and migrates into the remainder of the wick. Also, U.S. Pat. No. 4,366,241 discloses an apparatus provided for performing immunoassays employing a device consisting of a relatively small test zone referred to as an immunoabsorbing zone, and a relatively large liquid adsorbing zone in liquid receiving relationship with the immunoabsorbing zone. At least a portion of the liquid adsorbing member about the immunoabsorbing zone is enclosed in an impermeable enclosure. Presently available from Hybritech Incorporated is a product sold under the trademark ICON ®. It is described in detail in G. Valkirs, et al., Ser. No. 609,395, filed May 11, 1984, now U.S. Pat. No. 4,632,901, issued Dec. 30, 1986, and its continuation-in-part, Ser. No. 733,292, filed May 10, 1985, now U.S. Pat. No. 4,727,019, issued Feb. 23, 1988. The product employs a device which comprises a membrane having antibody fixed to its surface in conjunction with an absorbent member. The two components are enclosed in a container open at one end to permit sample to be applied to the membrane. The absorbent member, in capillary contact with the membrane, draws liquid through the membrane after it is applied. Air displaced within the body of the container by the addition of liquid passes through small ports located, for example, near the bottom of the container.

It is important that the moisture sensitive components of an apparatus for conducting immunoassays be protected from contact with contaminating moisture prior to use. A method presently used is to place the Hybritech Incorporated ICON ® product, referred to above, within a hermetically sealed pouch containing desiccants well known in the art. This particular method, although well suited for its particular purposes, is expensive, adds complexity to the packaging of the apparatus, and increases the size of the packaged product. Accordingly, an apparatus for conducting immunoassays which can be simply sealed from contaminating moisture would be desirable.

SUMMARY OF THE INVENTION

In its most general application, the present invention is directed to an improved apparatus for conducting ligand-receptor assay processes wherein the apparatus comprises a test zone to which is bound a receptor; a liquid absorbing zone in liquid receiving relationship with the test zone; and a container that is impervious to liquids which encloses the test zone and liquid absorbing zones. The improvement in the apparatus comprising a sealable opening in the apparatus to permit addition of assay reagents to the test zone and at least one vent port in communication with the sealable opening wherein the vent port provides a means for discharging from the container gas displaced from the liquid absorbing zone. The displaced air flows in a direction opposite to the flow of assay reagents.

In a more preferred embodiment, the present invention is generally related to the apparatus and method for conducting immunoassay processes of U.S. patent application Ser. No. 609,395 filed May 11, 1984, now U.S. Pat. No. 4,632,901, issued Dec. 30, 1986. To this end, an apparatus comprising an improved container is provided for conducting immunometric assays that does not require the use of a sealed pouch in order to protect the moisture-sensitive membrane of the apparatus during storage prior to use. The improved container is provided with at least one vent port in communication with the body of the container and the top of the container. Air displaced within the body of the container by the addition of liquid passes through said vent port located within the walls of the container to the top of the container. In this way the moisture-sensitive membrane may be protected by placing a removable, for example, peelable seal across the top of the container resulting in a smaller package form and decreased cost.

DETAILED DESCRIPTION OF THE PREFERRED EMBODIMENTS

Figures 1, 2:
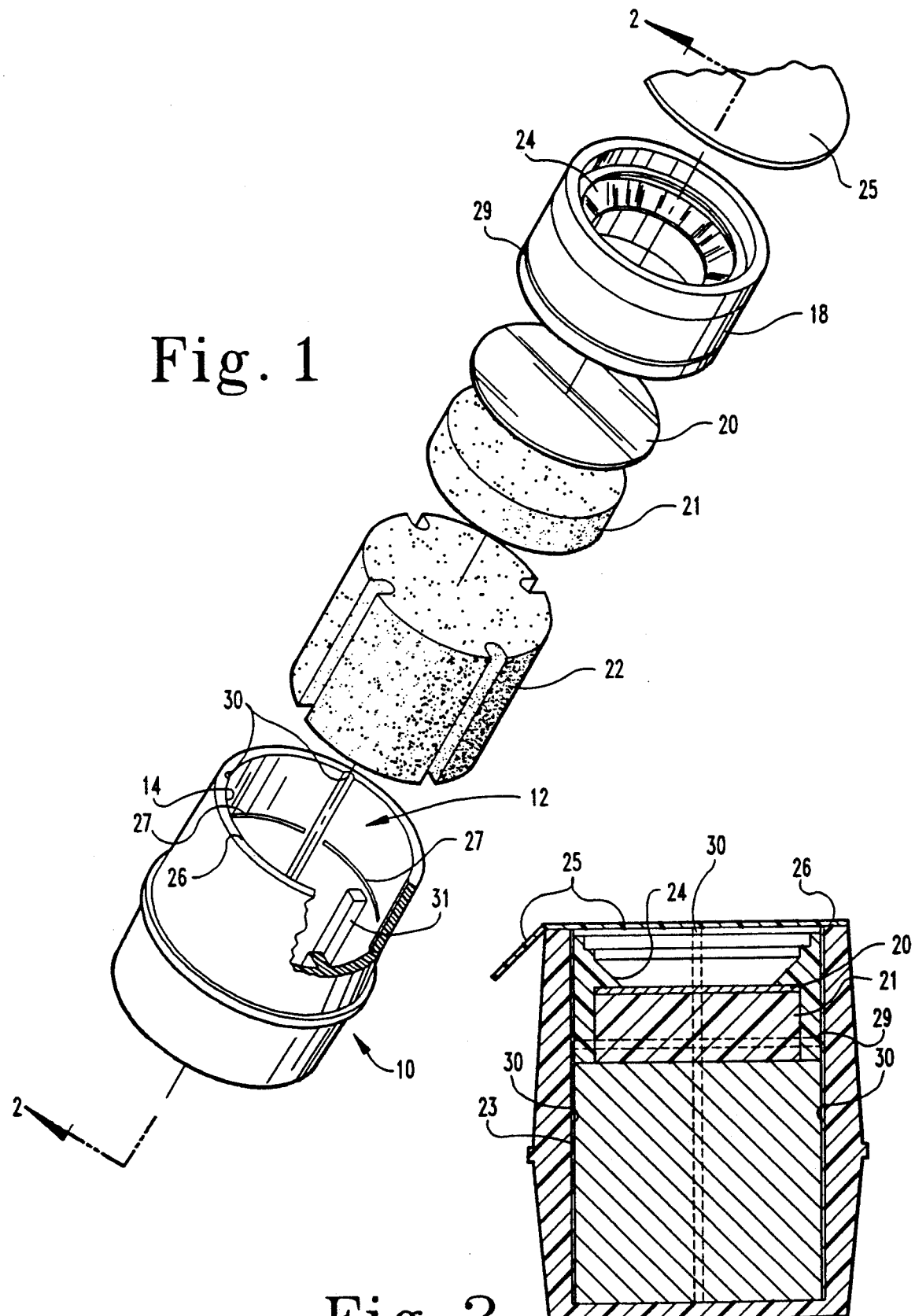
FIG. 1 is an exploded perspective view of the improved apparatus for performing an immunoassay, in accordance with the present invention.
FIG. 2 is a cross section taken along lines 2—2 of FIG. 1.

In its most general application, the present invention is an improvement in an apparatus for ligand receptor assays, said apparatus comprising a test zone to which is bound a receptor, a liquid absorbing zone in liquid receiving relationship with the test zone and a container that is impervious to liquids which encloses the test zone and liquid absorbing zone, wherein the improvement comprises an improved container provided with a sealable opening in the container to permit addition of assay reagents to the test zone and at least one vent port in communication with the sealable opening wherein the vent port provides a means for discharging from the container gas displaced from the liquid absorbing zone, the displaced gas flowing in a direction opposite the flow of the assay reagents upon addition. By providing a means for discharging the displaced air from the liquid absorbing zone in such a way that it channels the air flow in a direction opposite the flow of assay reagents, the place of discharge, i.e. the vent ports, can be located in close proximity to the opening in the apparatus to permit addition of assay reagents to the test zone. The closer in proximity these two openings are in the assay apparatus the easier, more convenient, and less expensive it is to seal both openings simultaneously and protect the moisture sensitive components of the apparatus. The prior art apparatus allows the displaced gas to flow in the same direction as the flow of the assay reagents which results in a discharge opening at some distance from the opening for addition of the assay reagents.

The present invention is an improvement in an apparatus for immunoassays, said apparatus comprising as a first member, a porous membrane or filter to which a receptor for a ligand or to which is bound an anti-receptor or which is capable of filtering cellular material from a sample being assayed if the ligand is associated with the cellular material, a second member which is an absorbent member having capillary passageways generally transverse to the upper and lower surfaces of said second member, and a container as set forth in greater detail in application Ser. No. 609,395, filed May 11, 1984, now U.S. Pat. No. 4,632,901, issued Dec. 30, 1986, and its continuation-in-part Ser. No. 733,292, filed May 10, 1985, now U.S. Pat. No. 4,727,019, issued Feb. 23, 1988, both incorporated by reference herein, wherein the improvement comprises an improved design comprising a sealable opening in said container to permit addition of assay reagents to said upper surface of said first member, and at least one vent port in communication with the body of the container and the top of the container. Air displaced within the body of the container by the addition of liquid passes through said vent port located within the walls of the container to the top of the container where the entire container including the vent port can be sealed with a single removable seal. Accordingly, the moisture-sensitive membrane may be protected by placing a removable seal across the top of the container resulting in a smaller package size and decreased cost.

As noted above, the apparatus of the present invention comprises, as a first member, a porous membrane or filter to which is bound a receptor for a ligand or to which is bound an anti-receptor or which is capable of filtering cellular material from a sample being assayed if the ligand is associated with the cellular material. In the latest case, the membrane or filter is selected to have a pore size which permits this separation. Any of a variety of filtering members may be used including glass fiber filters and filters of various synthetic or natural materials.

When the porous member has receptor bound to it, the receptor is selected for its ability to selectively bind directly with the target ligand. For example, if the ligand is an antigen, the receptor may be an antibody, preferably a monclonal antibody. If the target ligand is an antibody, the receptor may be an antigen or anti-antibody. If the ligand is an enzyme, the recept may be a receptor for the enzyme. If the ligand is a nucleic acid, for example, RNA or DNA, the receptor may be a complementary oligomer of DNA or RNA. In a preferred embodiment the first member is a membrane or filter to which an antibody preparation is covalently bound. Preferably the antibody preparation comprises a monoclonal antibody even though polyclonal antibodies from antisera may be used. Techniques for polyclonal and monoclonal antibody preparation are now well known in the art. For example, preparation of polyclonal antibodies is disclosed in Freund, J., and McDermott, K., *Proc. Soc. Exp. Biol. Med.*, 49:548 (1942) (describes use of Freund's "complete" adjuvant) and Freund, J. and Walter, A. W., *Proc. Soc. Exp. Biol. Med.*, 56:47 (1944) (describes use of Freund's "incomplete" adjuvant). The preparation of monoclonal antibodies is described in detail in Kohler, G., and Milstein, C., *Nature*, 256:495 (1975).

The material of the porous member is selected from a material to which the receptor or, if used, anti-receptor can be bound. In the case of protein receptors or anti-receptors, e.g., antibodies or antigens, a preferred material is nylon which has amino group residues or into which such groups have been introduced by chemical means, which permit a protein to be coupled to it by the well known glutaraldehyde method. Antibodies can be coupled to glass fibers through aminosilanes. Other natural or synthetic materials which can be coupled directly or through intermediates to a receptor may also be used.

The foregoing stresses chemical binding of the receptor or anti-receptor to the porous member. However, in appropriate cases the receptor or anti-receptor may be coated on the porous member or be a particulate which is entrapped within the interaction of the porous member. Therefore, as used herein, the term "bound" is intended to embrace any means for fixing receptor or anti-receptor to the porous member.

The second member is an absorbent member having capillary passageways generally transverse to the upper and lower surfaces. The second member is assembled with the first in a manner which permits direct communication between the pores or interstices of the first member and the capillaries of the second. Thus, as a liquid is applied to the first member and saturates it, the liquid is drawn into the absorbent member. As a result, flow can be induced through the first member when a liquid sample is applied to the upper surface of the first member even though the hydrostatic pressure of the fluid is so low that unaided it could not flow through the first member without the application of pressure to force it through or a vacuum to draw it through.

The selection of material for the second member is not critical and a variety of fibrous filter materials can be used. A useful material is cellulose acetate fibers oriented as in a cigarette filter. Those skilled in the art will appreciate that other absorbent members made of polyester, polyolefin or other materials may be used in place of cellulose acetate.

Turning now to FIG. 1, there is shown an exploded perspective view of the apparatus of this invention to perform immunoassays. Thus, in FIG. 1, a cylindrical container 10, although it may have any other appropriate shape, is closed at the bottom and is provided with an upper opening 12 defined by sidewall 14. The container may be made of glass or a suitable plastic material. As shown in FIG. 1, removable plug 18 is insertable through opening 12 in container 10 to permit insertion of the porous member 20, a circular membrane or filter disc, and an optional member 21, whose function is described below, which rest on cylindrical absorbent member 22, which is also inserted through opening 12.

A portion of removable plug 18 is constricted as shown in FIG. 1 by reference numeral 24 to provide an integral funnel to direct sample onto the member 20 and to assure that effective washing of sample and other add-ins onto the member 20 is accomplished.

The size of member 22, and, therefore, the volume of the portion of container 10 below the constriction is preferably selected so that all of the liquid to be added to the apparatus during an assay can be received in and retained in absorbent member 22. Means for venting air consisting of at least one vent port 23 (illustrated in FIG. 2) is provided. Vent ports 23 are formed of grooves 30 in container 10 which leave a space between the inner surface of container 10 and the outer surface of removable plug 18, to allow air displaced by the addition of liquid to escape the container 10 through opening 12. This improvement allows the venting of air displaced by the addition of liquid to the apparatus to be channeled and confined to an area defined by opening 12 in container 10. In this way the entire container 10 can be sealed from the environment with removable seal 25 removably attached over opening 12 of container 10 at surface 26. This seal may be made under such conditions of ambient moisture as are required. Requirements relating to moisture content of the sealed apparatus are well known in the art and hence are not further disclosed herein. Upon application of removable seal 25 as detailed above to container 10 having a closed bottom end as depicted in FIG. 2, a hermetic moisture resistant seal is obtained which may protect the contents of container 10 from contamination by exposure to moisture during the period of time from manufacture to use. As is well known in the art, removable seals such as removable seal 25 have the characteristic of being less expensive and less space consuming than pouch seals.

Protrusions 27 of container 10 engage annular groove 29 of removable plug 18 to lock removable plug 18 in place within container 10.

Supports 31 provide support to optional member 21, porous member 20 and removable plug 18 to prevent items 18, 20 and 21 from entering container 10 more than a desired amount.

In other aspects, the apparatus and its operation are similar to that described in U.S. patent application Ser. No. 609,395, filed May 11, 1984, now U.S. Pat. No. 4,632,901, issued Dec. 30, 1986, and its continuation-in-part, Ser. No. 733,292, filed May 10, 1985, now U.S. Pat. No. 4,727,019, issued Feb. 23, 1988, both hereby incorporated by reference.

Thus, an improved apparatus for use in performing immunoassays is disclosed which utilizes an improved design to allow the entire apparatus to be sealed by a single removable seal over the top. While embodiments and applications of this invention have been shown and described, it would be apparent to those skilled in the art that many more modifications are possible without departing from the present inventive concepts. The invention, therefore, is not to be restricted except in the spirit of the appended claims.

What is claimed is:

1. An apparatus for use in a ligand receptor assay process for the detection of a target analyte in a fluid sample, said apparatus comprising:
    a) a test zone to which is bound a receptor;
    b) a liquid absorbing zone, having a top surface, which is in liquid receiving relationship with said test zone;
    c) a single container that is impervious to liquids which encloses said test zone and said liquid absorbing zone;
    d) a sealable opening in said container to permit addition of assay reagents to said test zone; and
    e) at least one vent port, comprised of grooves located within the walls of said container, in close proximity to, and in communication with, said sealable opening and also in communication with said liquid absorbing zone wherein said vent port provides a means for discharging from said container gas displaced from said liquid absorbing zone, the flow of said gas being in a direction opposite to the flow of assay reagents through said liquid absorbing zone and not through the top surface of said liquid absorbing zone.

2. An apparatus according to claim 1 further comprising a removable seal sealing said sealable opening.

3. An apparatus according to claim 1 wherein said receptor is selected from the group consisting of an antibody and an antigen.

4. An apparatus according to claim 3 wherein said antibody is a monoclonal antibody.

5. An apparatus for use in a ligand-receptor assay process for the detection of a target analyte in a fluid sample, said apparatus comprising:
   a) a first member which is porous and to which is bound a receptor or which is capable of separating cellular material with which the ligand is associated from the fluid sample, which member has upper and lower surfaces;
   b) a second member which is a body of absorbent material having a top surface over which the first member is placed and having capillaries therethrough, which capillaries are in communication with the pores on the lower surface of the first member so as to draw fluid added to the upper surface which has permeated the first member into the capillaries of the second member;
   c) a single container that is impervious to liquids which encloses said first and second members;
   d) a sealable opening in said container to permit addition of assay reagents to said upper surface of said first member;
   e) a removable seal sealing said sealable opening; and
   f) at least one vent port, comprised of grooves located within the walls of said container, in close proximity to, and in communication with, said sealable opening and also in communication with said second member wherein said vent port provides a means for discharging from said container gas displaced from said second member, the flow of said gas being in a direction opposite to the flow of assay reagents through said second member and not through the top surface of said second member.

6. An apparatus according to claim 5 where the first member is a membrane or filter to which antibody against said target analyte is bound.

7. An apparatus according to claim 6 wherein said antibody is a monoclonal antibody.

8. An apparatus according to claim 7 wherein said membrane or filter is of a material selected from the group consisting of glass and nylon.

9. An apparatus according to claim 5 wherein said first member is a member capable of separating cellular material from the fluid sample.

10. An apparatus according to claim 5 wherein said first member is separated from said second member by a porous member.

11. An apparatus according to claim 5 wherein said sealable opening further comprises a section having sides which slope inwardly to define a funnel for direction of the added reagents onto said upper surface of said first member.

12. An apparatus according to claim 10 wherein said sealable opening further comprises a section having sides which slope inwardly to define a funnel for direction of the added reagents onto said upper surface of said first member.

13. An apparatus according to claim 5 wherein said first member is a porous matrix in which are entrapped microspheres to which are bound antibody against a target antigen.

* * * * *